(12) United States Patent
Greenwood et al.

(10) Patent No.: US 11,071,644 B2
(45) Date of Patent: Jul. 27, 2021

(54) CONTACT LENS PACKAGING

(71) Applicant: Greensmith Technologies Ltd, Taunton (GB)

(72) Inventors: Anthony John Greenwood, Richmond (GB); Guy St John Tristram Smith, Aldbourne (GB)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 220 days.

(21) Appl. No.: 16/076,936

(22) PCT Filed: Feb. 8, 2017

(86) PCT No.: PCT/GB2017/050309
§ 371 (c)(1),
(2) Date: Aug. 9, 2018

(87) PCT Pub. No.: WO2017/137738
PCT Pub. Date: Aug. 17, 2017

(65) Prior Publication Data
US 2019/0046353 A1 Feb. 14, 2019

(30) Foreign Application Priority Data

Feb. 9, 2016 (GB) ...................................... 1602335
Dec. 19, 2016 (GB) ...................................... 1621654

(51) Int. Cl.
*A61F 9/00* (2006.01)
*A45C 11/00* (2006.01)
*B65D 85/00* (2006.01)

(52) U.S. Cl.
CPC .......... *A61F 9/0061* (2013.01); *A45C 11/005* (2013.01); *A61F 9/0008* (2013.01); *B65D 85/00* (2013.01); *B65D 2585/545* (2013.01)

(58) Field of Classification Search
CPC .... A61F 9/0061; A61F 9/0008; A45C 11/005; B65D 2585/545
(Continued)

(56) References Cited

U.S. PATENT DOCUMENTS 3,490,806 A * 1/1970 Lopez-Calleja ...... A61F 9/0061
294/1.2
3,584,908 A 6/1971 Ray
(Continued)

FOREIGN PATENT DOCUMENTS

| CN | 1522131 A | 8/2004 |
|---|---|---|
| TW | 200930318 | 7/2009 |
| WO | 1999021519 | 5/1999 |

OTHER PUBLICATIONS

International Patent Application No. PCT/GB2017/050309, International Search Report and Written Opinion, dated Jun. 16, 2017.
(Continued)

*Primary Examiner* — Paul T Chin

(57) ABSTRACT

A contact lens applicator film (45) for picking up a contact lens (11) and applying the contact lens to an eye comprising: a sterilised film (45) wherein at least a portion of at least one side of the film comprises an adhesive coating that is arranged for adhering to the surface of a finger such that, in use, when applying the contact lens to the eye a user can pick up the contact lens applicator film with the finger and subsequently pick up the contact lens using the finger protected by the contact lens applicator film.

7 Claims, 11 Drawing Sheets

(58) Field of Classification Search
USPC .......................................................... 294/1.2
See application file for complete search history.

(56) References Cited

U.S. PATENT DOCUMENTS

| | | | | |
|---|---|---|---|---|
| 4,512,601 | A | 4/1985 | Jacobstein | |
| 4,691,820 | A * | 9/1987 | Martinez | B65D 75/326 206/205 |
| 5,031,622 | A * | 7/1991 | Lahaye | A61B 3/16 206/316.1 |
| 5,474,169 | A * | 12/1995 | Bauman | A45C 11/005 206/205 |
| 5,695,049 | A * | 12/1997 | Bauman | A45C 11/005 206/5.1 |
| 5,711,416 | A * | 1/1998 | Bauman | A45C 11/005 206/210 |
| 6,401,915 | B1 * | 6/2002 | Faxe | A45C 11/005 206/210 |
| 7,410,050 | B2 * | 8/2008 | Py | A45C 11/005 206/5.1 |
| 7,426,993 | B2 * | 9/2008 | Coldrey | B65D 75/366 206/5.1 |
| 7,819,241 | B2 * | 10/2010 | Post-Smith | B65D 75/327 206/5.1 |
| 7,850,002 | B2 * | 12/2010 | Newman | B65D 53/00 206/5.1 |
| 8,251,205 | B2 * | 8/2012 | Azera | A45C 11/046 206/5.1 |
| 9,095,195 | B2 * | 8/2015 | Mori | A45C 11/005 |
| 9,320,566 | B1 * | 4/2016 | Alston, Jr. | A61B 90/00 |
| 9,701,458 | B2 * | 7/2017 | Barrows | B65D 81/22 |
| 10,577,166 | B2 * | 3/2020 | Barrows | B65D 81/22 |
| 2002/0158477 | A1 * | 10/2002 | Faxe | A61F 9/0061 294/1.2 |
| 2002/0163212 | A1 * | 11/2002 | Py | A61F 9/0061 294/1.2 |
| 2005/0103649 | A1 | 5/2005 | Vulcu et al. | |
| 2006/0260956 | A1 * | 11/2006 | Stachowski | B65B 25/008 206/5.1 |
| 2007/0164576 | A1 | 7/2007 | Kim | |
| 2008/0011619 | A1 * | 1/2008 | Newman | A45C 11/005 206/5.1 |
| 2008/0170201 | A1 * | 7/2008 | Filippo | G02B 1/043 351/159.33 |
| 2009/0121370 | A1 * | 5/2009 | Barrows | B29C 33/40 264/2.5 |
| 2015/0000797 | A1 * | 1/2015 | Sebald | C22C 38/002 148/518 |
| 2015/0173474 | A1 * | 6/2015 | Barrows | B65D 81/22 206/5.1 |
| 2016/0198825 | A1 * | 7/2016 | Fawdington | A61F 9/0061 206/5.1 |

OTHER PUBLICATIONS

International Patent Application No. PCT/GB2017/050309, Invitation to Pay Additional Fees and, Where Applicable, Protest Fee and Partial Search Report, dated Apr. 24, 2017.
China Patent Application No. 201780009263.0, Office Action, dated Dec. 30, 2019.

* cited by examiner

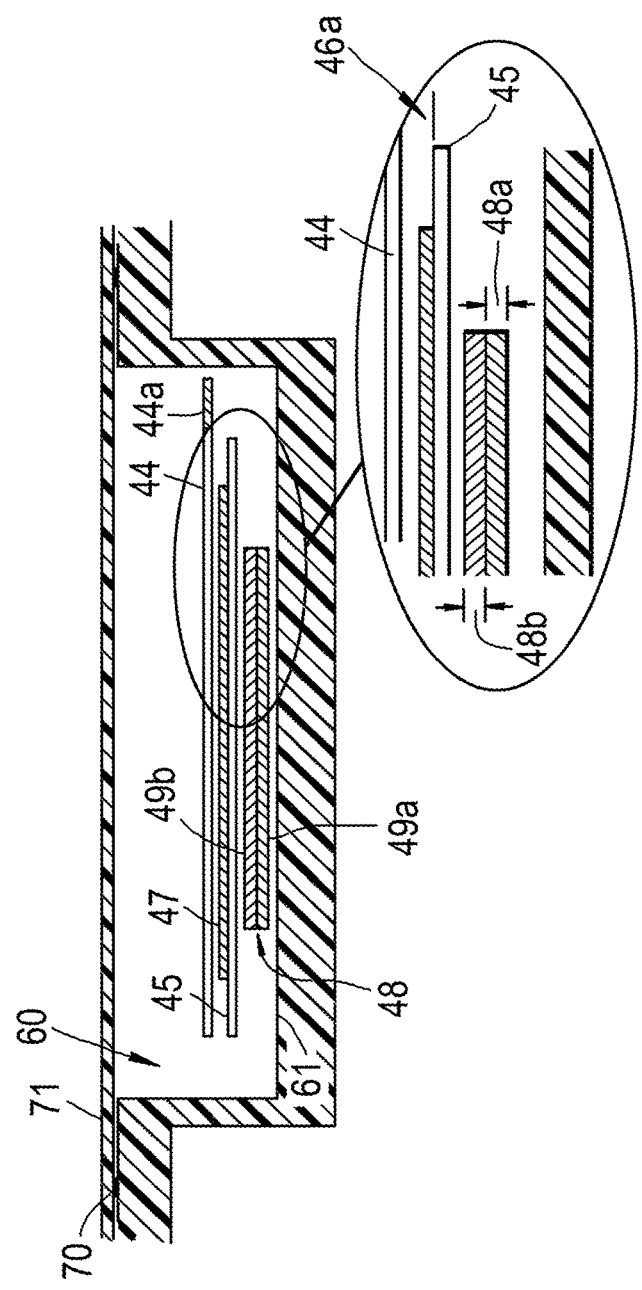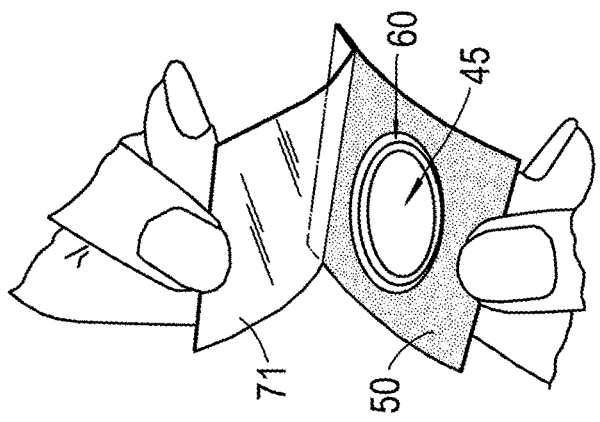

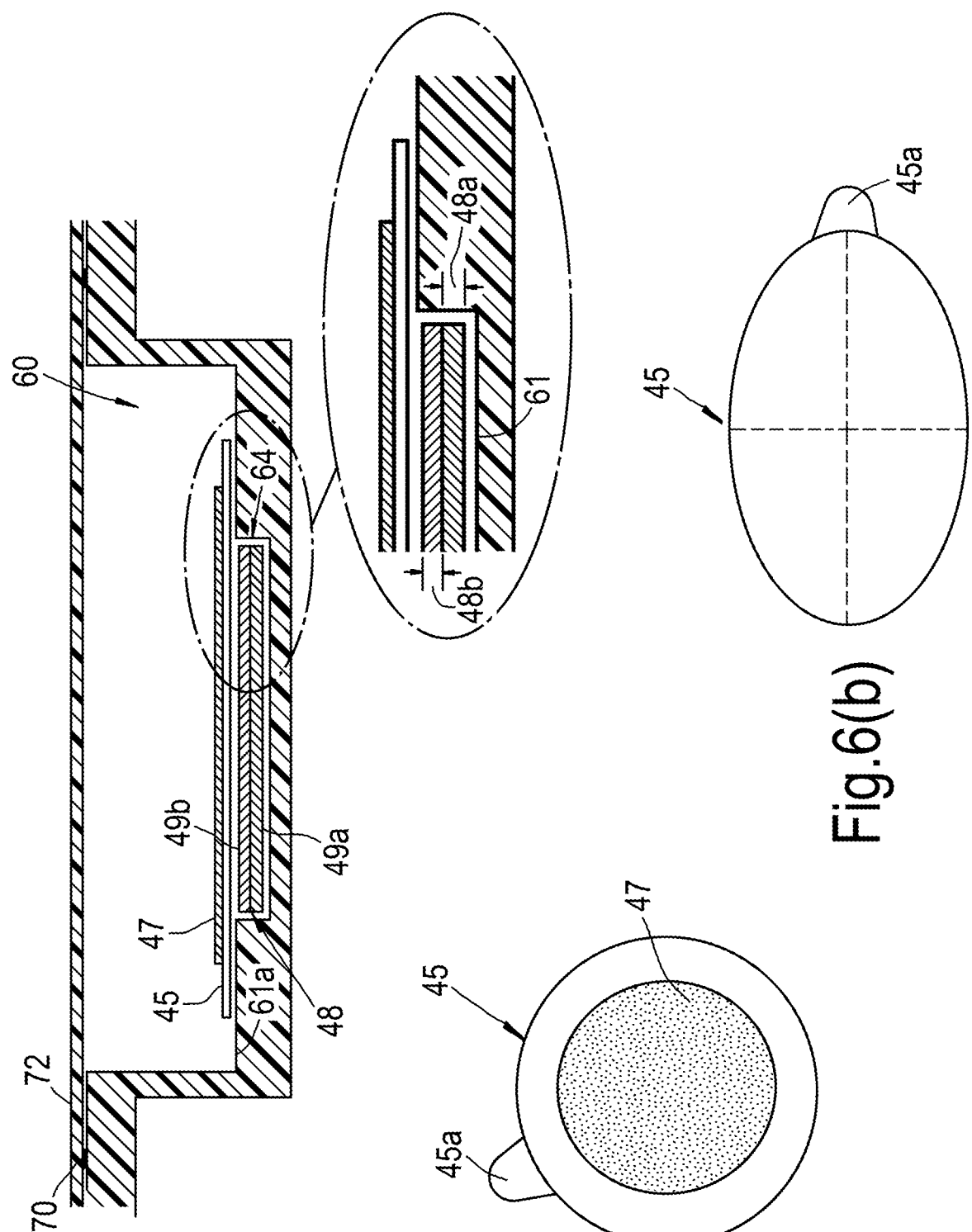

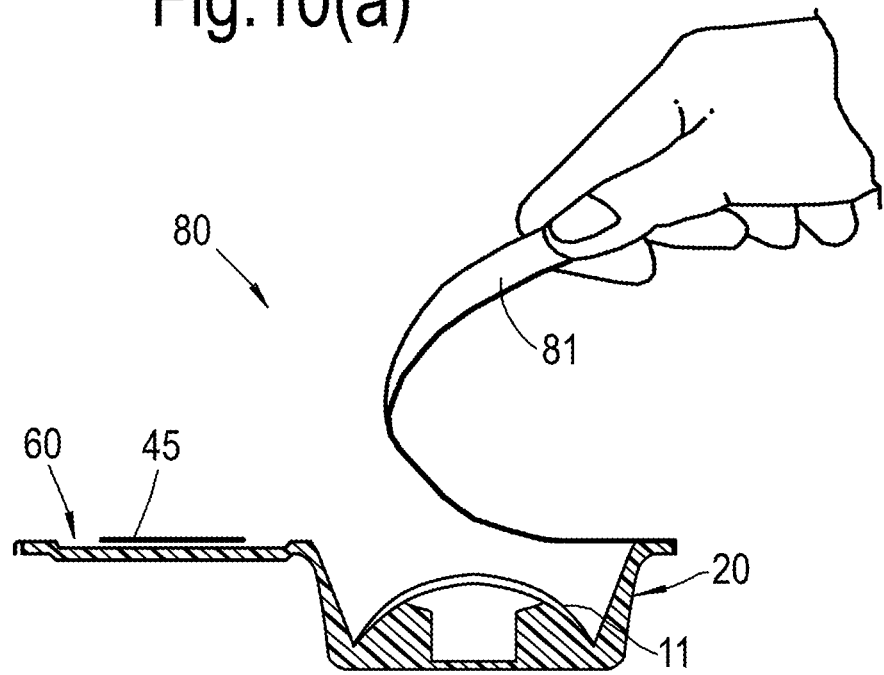

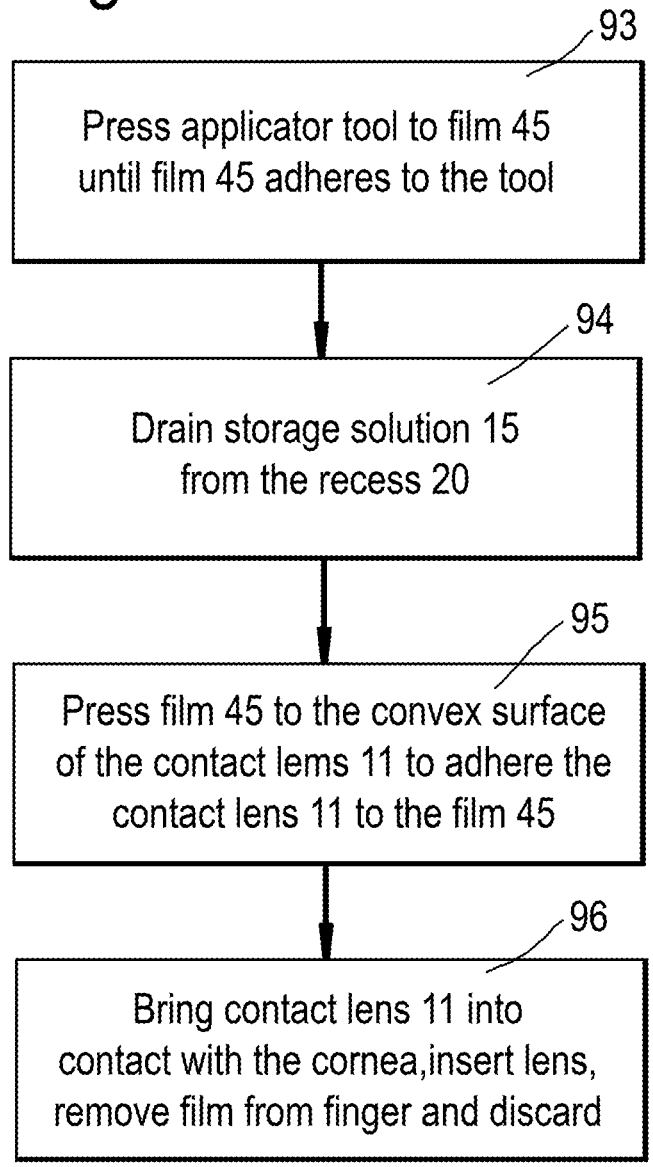

CONTACT LENS PACKAGING

CROSS-REFERENCE TO RELATED APPLICATIONS

This application is a national phase entry under 35 USC § 371 of International Patent Application PCT/GB2017/0503099 ("the '099 application"), filed on Feb. 8, 2017, which claims priority to United Kingdom Patent Application No. 1621654.1 ("the '541 application"), filed on Dec. 19, 2016 and United Kingdom Patent Application No. 1602335.0 ("the '350 application"), filed on Feb. 9, 2016. The '099 application, the '541 application, and the '350 application are hereby incorporated in their entireties by this reference.

TECHNICAL FIELD

The present invention relates to a storage container for a contact lens, more particularly a storage container fabricated to support the corneal contact surface of the lens. The present invention also relates to a contact lens applicator, more particularly a terminally sterilised disposable applicator for handling a contact lens.

INTRODUCTION

The present invention relates to contact lens storage containers, and more particularly to disposable storage containers for contact lenses. Many different types of containers have been used for storage of contact lenses. Some of these are relatively durable moulded structures intended for repeated use and include replaceable covers. Others are relatively low cost disposable structures for storage of the lens prior to use by a wearer. As packaging adds to the overall cost of the lens, it should be made as economically as possible but without compromise to the requisite packaging criteria. The traditional blister pack packaging for disposable lenses consists of a polypropylene receptacle for the lens (referred to as a cartridge), sealed by a removable lid typically made of foil. The cartridge is usually an injection moulded plastic which has high stiffness but is capable of limited plastic deflection and includes a pre-formed well. The cartridge is filled with a suitable storage solution, preferably saline, and receives a single lens into the well. The well is then sealed and sterilised (or 'autoclaved') using steam and pressure to achieve terminal sterilisation as demanded by industrial standard requirements, other methods of sterilisation exist including irradiation.

The lens within a cartridge must be kept hydrated; the package must therefore be kept sealed and should eliminate water vapour transmission through the cartridge and the seal to maximise the shelf life and prevent drying out of the lens.

There exists a variety of contact lens cartridges, including pre-formed blister packs. As exemplified in the prior art, conventional cartridges are designed to support the immersed lens in one of two orientations. Firstly, the convex surface of the lens is supported such that it extends towards the film cover; in the second, more commonly used orientation, the concave (corneal contact) surface of the lens is supported such that it extends towards the film seal. It is not unknown for a contact lens cartridge to offer no direct support to a lens in regards to which surface is extended towards the foil cover, however, in these cartridges it is common for the lack of support to result in the inversion or folding of the lens which can easily result in incorrect application and thus use of the lens. Cartridges that support the lens do so through a variety of means. One such means is to fabricate the well, in a cartridge during the injection moulding process, so that its shape supports either the convex or concave surface of the lens as taught in BAUMAN (U.S. Pat. No. 5,474,169). Wherein a concave support structure gives rise to the convex surface of a lens being extended towards the foil seal. Problems associated with these designs include the lens becoming attached to the walls of the well through high surface tension forces resulting in the need for excessive manipulation of the lens to remove it from the well which is not hygienic for the wearer through increased handling of the contact lens. MENICON (TW Pat. No. 200930318) discloses a separate restoration member comprising a foam or sponge structure located underneath a contact lens in a packaging such that when the packaging is sealed, the lens and sponge are compressed but on opening the package, the sponge decompresses and causes the lens to be return to a curved shape. In MENICON, the lens is removed by making a pinching action at two distinct points-of-contact on the contact lens. This pinching motion exposes the lens to more manipulation which increases the risk of contamination. The restoration member can comprise a central cavity so as to reduce the contact area of the lens with the sponge and facilitate the motion of air under the rim of the contact lens.

An alternative means for supporting a lens whereby removal only involves a single point-of-contact in a given orientation includes fabricating a support lattice which accommodates the contours of a lens. The support lattice can be inserted into the well of the cartridge and against it a lens may rest as is demonstrated in the 'dome' of VULCU (US Pat. No. 20050103649). These lattice structures can, to an extent, prevent the lens from sticking to the support structure however, complete prevention is not possible. Google Inc. (US Pate No. 2015/0173474) teaches a pedestal disposed within a contact lens container for contacting the concave side of the contact lens comprising an annular ring. The annular ring has a first end attached to the base of the container and is divided into a plurality of spaced apart segments having a major axis that extend circumferentially to form the annular ring and axially towards the base of the container. The second end of the annular ring opposite the first end may have inclined surfaces that conform to the curvature of the concave side of the contact lens.

There is therefore a need for a contact lens storage container that facilitates an increased ease of lens removal such that problems traditionally associated with high levels of surface tension are avoided whilst providing a container that supports the lens in-situ so as to make application require less manipulation of the lens and thereby, reducing problems associated with hygiene.

To prevent contamination of the contact lens, they are stored in a sterile solution in a sealed container. In traditional use, a user breaks the seal by peeling-back the foil cover to expose the immersed lens. Users can opt to remove the sterile solution within the well before application, with for example an absorbent material or a drainage font used to pour the solution from the container, or begin application with the lens being immersed. The point of application is the moment contamination risk is highest. Users that apply the contact lens to their eye through manual manipulation using their fingers are encouraged to adopt recommended hygienic procedures by the contact lens practitioner which involves thoroughly washing and drying their hands before making contact with the lens surfaces.

Incomplete or inadequate washing results in microbial and mechanical debris coming into contact with the contact lens thus increasing the risk of eye infections as well as scratching to the cornea through mechanical corneal abrasions. Despite adequate care being taken to ensure that the appropriate hygienic procedures are adhered to when applying contact lens, there still exists the problems of discomfort and corneal scarring from infection through contact lens usage, particularly regular usage, through infection resulting in increased irritation for the wearer.

Damage to the corneal surface may produce acute irritation, pain, redness or watery eyes and make the cornea more susceptible to infection. Furthermore, manual manipulation increases the risk of dropping, inverting or even folding-over of the lens thus leading to more manipulation and therefore further increases the risk of contamination. Infection of the cornea (infectious keratitis) may lead to mild, moderate or severe permanent visual loss. Organisms associated with severe visual loss include: *pseudomonas*, streptococci, fungi and *acanthamoeba*. In an attempt to mitigate the risk of infection through manual manipulation, manufacturers have developed mechanical tools such as that found in VULCU. These tools grip the contact lens with suction thus reducing the possibility of contamination through inadequate hand washing. Problems associated with these tools include: loss of dexterity in comparison to the human hand, contamination through inadequate cleaning of the tool and time for successful application. These tools are also only free from manual manipulation if the lens within a container is situated with the required orientation within the storage container to match the suction head on the tool. Similarly, Kim (US Pat No. 2007/0164576) teaches a tool or contact lens device for handling the contact lens comprising a lens support having a concave surface that is treated or modified to hold the contact lens and a handle or stem coupled to the lens support for positioning the lens support during the process of inserting or removing a contact lens from a wearer's eye. The concave surface of the lens support is treated or modified to provide a gripping or adhesive property that overcomes a contact lens-to-eye surface tension during removal of a contact lens. A protective layer is coupled to or contacts the treated or modified surface of the lens support. The protective layer functionally protects or isolates the treated or modified surface. The surface of the protective layer has a capillary action property that is sufficient to hold or grip a contact lens, and also to release and transfer a contact lens when the contact lens comes in contact with a wearer's eye during a contact lens insertion procedure. The tool or contact lens device is also used to remove a contact lens from the wearer's eye which involves removing the protective layer from the contact lens device, thereby exposing the modified surface of the lens support for gripping or adhering to the contact lens.

Again, Kim suffers from same problems as Vulcu in respect to the use of tools to apply the contact lens to the wearer's eye. Further problems include the bulkiness of the tool preventing storage within a traditional contact lens container. Contact lenses, particularly daily disposable contact lenses are manufactured in bulk; thus, any significant alteration to the tooling to the containers for storing the contact lens would incur significant tooling costs. Moreover, significant alteration to the container for storing the contact lens would lose the compact nature of the contact lens container, and therefore its desirability. Jacobstein (U.S. Pat. No. 4,512,601) teaches a device in the form of a rigid disk having a thickness that is sized to maintain a sufficient distance between the surface of the eye and the fingertip. The relatively large thickness of the applicator device is to mitigate the risk of abrasion or contamination in the eye, particularly in the case of fingers with long fingernails or a person of low dexterity. The front face of the device for picking up the contact lens comprises a central circle aperture having a diameter to support the structural shape of the contact lens, and to maintain its shape during transfer to the eye. An adhesive layer is attached to the bottom of the disc for adhereing onto a finger of the user. Again significant alterations are needs to the contact lens container for accommodating the disc. There is therefore a need for a contact lens applicator and method for use that solves the issues detailed above in regards to minimising contamination risk commonly present during manual manipulation or manipulation using a mechanical tool whilst being quick and simple in terms of use.

SUMMARY OF THE INVENTION

The present invention is concerned with the reduction of contamination risk when handling a contact lens. The present applicant has mitigated the above problems by providing
a contact lens applicator film for picking up a contact lens and applying the contact lens to an eye comprising:
a sterilised film wherein at least a portion of at least one side of the film comprises an adhesive coating that is arranged for adhering to the surface of an applicator tool (e.g. finger) such that, in use, when applying the contact lens to the eye a user can pick up the contact lens applicator film with the finger and subsequently pick up the contact lens using the finger protected by the contact lens applicator film.

By providing an intermediate sterilised barrier between the applicator tool (e.g. finger) and the surface of the contact lens, contaminants are prevented from passing from the applicator onto the eye. The film is deformable so that it conforms to the application tool, whether that be an index finger or another mechanical device. The applicator film provides a thin, sterile coating to the finger so as to prevent microbial, mechanical and chemical contaminants from transferring to the contact lens, and thereby being transferred to the eye causing mechanical contamination or microbial contamination. The corneal surface tends to be more dome shaped or pronounced in comparison to the rest of the eyeball surface. The cornea does not contain any blood vessels, but instead contains many nerve endings that make it extremely sensitive. Proper positioning of the contact lens on the corneal surface of the eye is important to allow light to enter and be focussed by the eye. Improper positioning of the contact lens on the eye, e.g. on the sclera, can result in the contact lens migrating and being trapped under the eyelid when the wearer subsequently blinks resulting in the contact lens creasing on the surface of the eye and thereby, preventing the contact lens from focussing the light through the cornea. Moreover, improper positioning of the contact lens on the corneal surface of the eye increases the tendency to cause irritation since a scratch or a loose contact lens on the cornea can be painful. The film allows the user to apply the contact lens to the eye whilst still maintaining the sense of touch and feel of the contact lens with the finger when touching the surface of the eyeball, particularly when offering the contact lens to the corneal surface of the eye. The sense of touch offerd by the applicator film allows the user or wearer to properly position the contact lens onto the corneal surface of the eye. In some instances, the wearer can re-position the contact lens on the eye surface until he/she feels the corneal surface which has a different feel to the sclera. The applicator film of the present invention mitigates significant loss of sense of touch of the finger when applying the contact lens to the eye.

To apply the applicator film onto the finger, at least a portion of at least one side of the film comprises an adhesive coating such that the film adheres to the finger when contact is made. To prevent adhesive residue being present on the surface of the contact lens which would obscure vision, the side opposite the adhesive coating is free of adhesive. The present invention relies on surface tension as a result of the fluid used for storage of the contact lens for adhesion between the surface of the contact lens and the applicator tool. For example, the surface of the applicator film has a capillary action property sufficient to adhere onto the surface of the contact lens. However, in extreme sporting or windy environments, it is sometimes beneficial to ensure that the lens does not fall from the finger. To permit a stronger adhesion between the surface of the contact lens and the film, both opposing sides of the film comprises an adhesive coating; the adhesive coating on one side of the applicator film is used to pick up the film and the adhesive coating on the opposing side is used to pick up the contact lens. Furthermore, the adhesive coating between the surface of the contact lens and the film may be water soluble, preferably soluble in eye fluid, to prevent any adhesive residue obscuring the user's vision. To permit the contact lens to release from the finger protected by the applicator film of the present invention at the moment the contact lens is inserted onto the surface of the eye, the surface tension between the contact lens and the applicator film is less than the surface tension between the contact lens and the eye, i.e. the contact lens-to-eye surface tension overcomes the surface tension between the applicator film protecting the finger and the contact lens because the area of contact between the contact lens and the cornea is greater than the area of contact between the contact lens and the applicator film, as is the case when applying a contact lens without an applicator film.

To permit easy removal of the film from the finger for disposal, the adhesive coating in contact with the finger does not extend across the entire surface area of the film but rather occupies a smaller area primarily used to pick up the film. Preferably, the side of the film in contact with the finger comprises an inner portion and an outer portion, whereby the inner portion comprises the adhesive coating and the outer portion, which is free from the adhesive coating, comprises a tab for removing the film from the applicator tool, e.g. index finger.

To ensure sterility of the film, the present invention provides a contact lens applicator container for housing at least one contact lens applicator film. Preferably, the contact lens applicator container comprises a recess having a base wall for housing the at least one contact lens applicator film. As the film is very thin, it is prone to curling when stored in the container and thus, in order to maintain the orientation and structural integrity of the film (e.g. flatness) within the container such that the side of the film comprising the adhesive coating for contact with the applicator is presented to the user when the container is opened, and to prevent curling of the film, the base of the container comprises a pressure sensitive adhesive. The adhesive properties of the adhesive coating on the film are chosen such that the bond strength between the applicator tool (e.g. finger) and the film is stronger that the bond strength between the pressure sensitive adhesive coating on the base of the container and the film. This permits the film to be easily removed from the container whilst ensuring that there is no adhesive residue from the base being transferred to the film. To ensure that the applicator film substantially conforms to the contour of the finger to be protected by the applicator film of the present invention, a rolling action of the finger is generally required to maximise the contact surface area of the adhesive coating of the applicator film with the finger. To mitigate the need to roll the finger over the adhesive coating of the applicator film, optionally the base wall of the recess housing the applicator film is deformable so as to conform to the contour of the finger under the application of finger pressure. Thus, instead of or to minimise the amount of rolling action of the finger, the base wall of the recess deforms under the application of finger pressure causing the applicator film housed therein to conform to the contour of the finger. Preferably, the base wall of the recess is composed of a deformable material or alternatively, inorder to maintain the manufacturing efficiency, the thickness profile of the base wall is predetermined so that it is deformable under the application of pressure by the finger. In an example of the present invention, the base wall is thinner than the rest of the applicator container.

It is important that the surface tension forces associated with the fluid for storing the contact lens between an applicator tool (e.g. finger) and the surface of the contact lens is not only sufficient to lift the contact lens from the storage container but also strong enough when the contact lens is offered up to the eye. The surface tension and thus, the adhesion of the surface of the contact lens to the applicator tool is dependent on the contact surface area between the applicator tool and the surface of the contact lens. In existing systems, whereby the contact area between the applicator tools such as the index finger and the contact lens is not controlled, the adhesion (e.g. surface tension forces) between the surface of the contact lens and the applicator tool can result in the contact lens inverting from its preferred orientation for insertion onto the eye, thus requiring additional manual handling in particular to the corneal contacting surface. Increased manual handling not only results in increased contamination risk but it also increases the potential for lens damage such as creases as a result of folding. Moreover, by controlling the contact surface area between the contact lens and an applicator tool reduces the extent of contaminant exposure from the applicator tool to the contact lens. For example, where the applicator tool is an index finger, the increased contact surface area between contact lens and the index finger may result in a greater level of contaminant from the index finger passing onto the contact lens surface.

In a further aspect of the present invention a storage container for contact lenses is provided comprising:

i) at least one well for receiving a contact lens and storage liquid, the well having a floor;

ii) a support structure for holding the contact lens in a defined location above the floor of the well, the defined location comprising lens depression area that in use permits depression of the contact lens under finger pressure;

iii) a guide capable of engaging the contact lens edge when a contact lens is inserted into the well and to urge the contact lens to lie within the defined location and over the depression area.

To ensure adequate adhesion (e.g. as a result of the surface tension from the storage contact lens fluid) between the index finger and the surface of the contact lens for picking up the contact lens, the contact surface area between the contact lens and the applicator tool (e.g. finger) is controlled by the portion of the contact lens over a depression area. The size of the depressed area is controlled since if it is too small the surface tension between the finger and contact lens will not be greater than between the contact lens and the support. If, however, the depressed area is too large then the lens is at risk of collapsing or inverting. The optimum ratio is such that the surface tension of the part of the contact lens that is depressed is large enough for it to adhere to the finger and the surface tension between the support structure and the remainder of the contact lens outside of the depression area is sufficient to hold the lens in place in the correct orientation. However, whilst controlling the contact surface area beween an applicator tool and the surface of the contact lens is important to ensure adequate surface tension for picking up the contact lens from its storage container and yet be released when applied to the corneal surface of the eye (i.e. the lens-to-eye surface tension overcomes the surface tension between the applicator tool and the contact lens), the correct positioning of the contact lens on the surface of the applicator tool, in particular the tip of the finger, is also important to ensure the correct placement of the contact lens on the corneal surface of the eye. The applicator tool is for example, a finger protected by the applicator film of the present invention. Correct placement of the contact lens on the surface of the finger protected by the film of the present invention, for example, also ensures that the apex of the contact lens is correctly aligned with the corneal surface of the eye as well as improving the ease by which the contact lens is applied to the eye. For example, in the case where the contact lens is incorrectly placed on the finger would in a majority of cases necessitate the user to re-position the contact lens on the finger resulting in increased handling of the contact lens and thus, increased risk of contamination. To ensure that the contact lens, in particular the apex of the contact lens is correctly positioned on the surface of the finger, e.g. the tip of the finger, it is necessary to correctly position the contact lens on a support structure of the storage container, in particular the lens depression area of the support structure that permits depression of the contact lens under finger pressure. Incorrect positioning of the contact lens on the support structure, in particular the depression area, results in incorrect positioning of the contact lens on the finger with the resultant problems described above.

The present applicant has mitigated the above problem, by providing a guide capable of engaging the contact lens edge when a contact lens is inserted into the well and to urge the contact lens to lie within a defined location and over the depression area. Preferably, the guide urges the contact lens centrally over the depression area. More preferably, the depression area comprises an unsupported portion of the support structure. The depression area has a range between 5 mm$^2$ to 180 mm$^2$, preferably 78 mm$^2$.

The support structure comprises a profile for supporting the concave surface of the contact lens, i.e. the contact lens is orientated in the storage container such that the convex side of the contact lens is facing the wearer and the guide comprises a profile for guiding the contact lens over the depression area. The support structure is profiled to allow the contact lens to deform about a fulcrum when pressure is applied to the portion of the contact lens in the depression area. Preferably, the profile of the guide extends outwardly from the support structure. More preferably, the profile of the support structure and the profile of the guide meet at a substantially 'V' shaped configuration. The support structure and the guide cooperate so as to urge the contact lens substantially centrally over the depression area of the support structure.

To maintain a pressure equilibrium between the outside surface of the contact lens and underneath the contact lens, and thereby prevent the contact lens from collapsing onto the support structure at the moment the storage fluid is poured from the storage container, the support structure holds the contact lens above the floor of the well so as to create a path for air to flow underneath the contact lens. Without the rapid influx of air underneath the contact lens when the storage fluid is poured from the container, a pressure differential can exist as a result of a drop in pressure (or vaccum effect) underneath the contact lens causing the contact lens to collapse around the support structure under atmospheric pressure.

To prevent the contact lens from inverting during the application of finger pressure, as well to control the surface area contact between a finger protected by the applicator film of the present invention and the portion of the contact lens in the depression area, the profile of the support structure may extend between the fulcrum and the guide such that the distance between a point on the guide and the fulcrum is less than or equal to the length of the contact lens that is in contact with the profile of the support structure. The profile of the support structure and the profile of the guide cooperate to define a seat for supporting the rim of the contact lens and thereby, resist the contact lens from inverting when pressure is applied to the portion of the contact lens in the depression area. By having the distance between a point on the guide to the fulcrum less than the length the contact lens is in contact with the profile of the support structure ensures that the contact lens is prevented from inverting when pressure is applied to the portion of the contact lens in the depression area since any attempt to invert the contact lens, the outer rim of the contact lens would foul or touch against a point on the guide. Contact of the outer rim of the contact lens to a point on the guide also controls the finger pressure necessary for picking up the contact lens.

The guide is profiled to extend outwardly from the support structure e.g. an outwardly inclined surface so as to ensure that the contact lens lifts clear from the storage container without impinging or fouling against the walls of the well. For manufacturing efficiency, preferably the well comprises an upwardly extending sloping peripheral wall, more preferably, the wall of the well is profiled as the guide.

To reduce the adhesion and thus, surface tension between the contact lens and the support structure, thereby enabling the contact lens to be easily lifted off the supporting member, the contact surface area between the support structure and the contact lens itself is made small. Preferably the support structure comprises a plurality of spaced apart fins extending from one or more walls of the well. More preferably, the plurality of spaced apart fins extends upwardly from the floor of the well. The space between the fins provide ventilation channels to allow air to enter through the channels during removal of the contact lens and thereby, prevent the lens from sticking to the well or support structure. The channels between the fins also prevent the storage solution from being trapped within the support structure enclosure. Without the channels, or spacing between the fins, a vacuum suction effect can be created during the depression of the contact lens as discussed above, resulting in the contact lens collapsing around the fins and thereby, increasing the amount of manipulation of the lens to lift the lens from the support structure. Optionally, the fins comprise the guide; more preferably, each of the plurality of spaced apart fins comprises a first profile for supporting the concave surface of the contact lens and a second profile for guiding the contact lens over the depression area. In comparison to the annular ring discussed in Google Inc. (US Pate No. 2015/0173474), the first profile of each of the plurality of spaced apart fins cooperate to provide improved support to the concave side of the contact lens and thereby, minimise the ability the contact lens from collapsing around the support structure through a vaccum generated during drainage of the contact lens storage solution. The present applicant has found that having the support structure shaped as an upstanding annular ring suffers from the problem of little or no support to the concave side of the contact lens resulting in collapse of the contact lens around the upstanding annular ring removing the ability to remove the contact lens from its storage container easily. The presence of a plurality of spaced apart fins extending from one or more walls of the well, not only provides improved support to the concave side of the contact lens but also the plurality of the fins also provide the advantages of a depression area to control the contact surface area of the contact lens with the applicator tool (e.g. finger protected by the film of the present invention). For example, each of the plurality of radially spaced apart fins can partially extend from one or walls of the well to provide a region where the contact lens is left unsupported, e.g. the depression area.

To provide an all in one solution for minimising cross contamination from the applicator tool to the eye through manually handling the contact lens, the present invention provides a kit. The kit comprises the contact lens applicator film as described above and a contact lens container as described above. The kit can optionally provide a contact lens applicator container as described above, preferably the kit is formed as a single body. The all in one solution not only provides a container that controls the contact surface area between the contact lens and the applicator tool so as to minimise or reduce the level of cross contamination from the applicator tool (e.g. finger) to the contact lens as well as providing ease of removal of the contact lens from the container but the addition of the contact lens applicator film that acts as a sterile barrier between the applicator tool (e.g. finger) and the contact lens removes any possibility of cross contamination from the applicator tool (e.g. finger) passing onto the contact lens. Moreover, the contact lens applicator film maintains the applicator tool (e.g. finger) in a hygienic or sterile condition. Whilst adopting appropriate hygenic procedures when applying contact lens to the eye, the present invention removes the need to adopt rigorous hygiene procedures needed to ensure safe use of contact lens that is free from the risk of eye infections as recommended by the contact lens practitioner and manufacturer.

BRIEF DESCRIPTION OF THE DRAWINGS

Further preferred features and aspects of the present invention will be apparent from the claims and the following illustrative description made with reference to the accompanying drawings in which:

FIG. 3(*d*) shows a top view of the contact lens storage container according to another embodiment of the present invention.

FIG. 3(*e*) is a side view of the support structure comprising fins for supporting the concave side of the contact lens over the depression area.

FIG. 3(*f*) is a side view of a fin shown in FIG. 3(*d*) for supporting the curvature of the concave side of the contact lens.

FIG. 4 is a view of a contact lens applicator film housed in a container according to an example of the present invention.

FIGS. 5(*a* and *b*) show cross-sectional views each with an expanded sectional view of a contact lens applicator film housed in the container as shown in FIG. 4 according to different examples of the present invention.

FIG. 6*a* is a top view of a contact lens applicator film according to an example of the present invention.

FIG. 6*b* is a top view of a contact lens applicator film according to an example of the present invention.

FIG. 9(*e*) shows the deformation of the base wall of the well to conform to the curvature of the finger when picking the applicator film of the present invention.

FIG. 10(*b*) is a schematic representation of a kit comprising a contact lens applicator film and contact lens storage container according to an example of the present invention.

FIG. 10(*c*) is a schematic representation of the underside of the kit shown in FIG. 10(*b*).

FIG. 10(*d*) is a schematic representation of the container for housing the applicator film of the present invention.

FIG. 12 shows the steps in applying a contact lens stored in the kit shown in FIG. 10 and FIG. 11.

DETAILED DESCRIPTION

Figure 1:
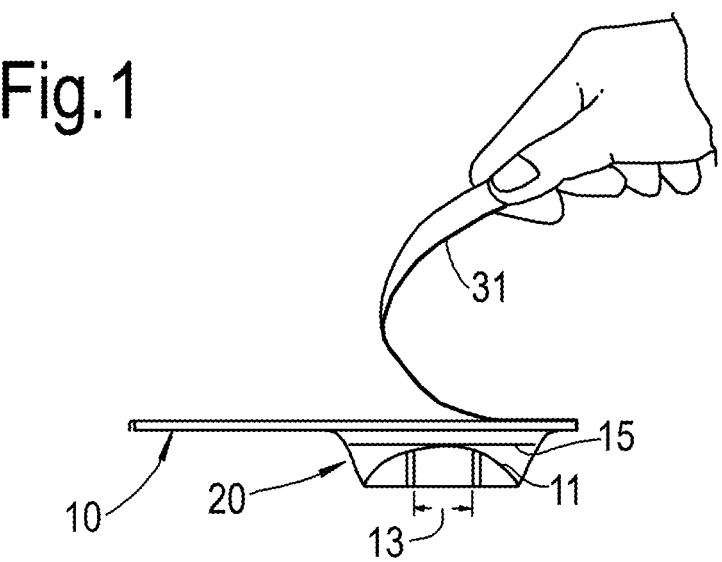
FIG. 1 is a cross-sectional view of a contact lens storage container according to an example of the present invention.

For the purpose of description in a specific embodiment of the present invention, a storage container 10 is configured for use with a contact lens 11 as seen in FIG. 1. The contact lens 11 housed in a cartridge storage container 10 can be fabricated of any suitable material known in the art; the two general categories of lens are soft or rigid gas permeable lenses, the use of each category is dependent on mix of user choice and lens function. It should be appreciated that the storage container 10 may house at least one contact lens 11.

The storage container 10 can be fabricated individually or as part of blister pack packaging (not shown) comprising a plurality of cartridges 10. The storage container 10 is fabricated of a material with a high stiffness whilst being capable of limited plastic deflection and water-tight; typically this can be a plastic. The storage container 10 can be manufactured with any suitable means, the most usual being injection moulding although thermoforming and compression moulding may be used. Optionally the storage container 10 is formed as a single body.

Figure 2:
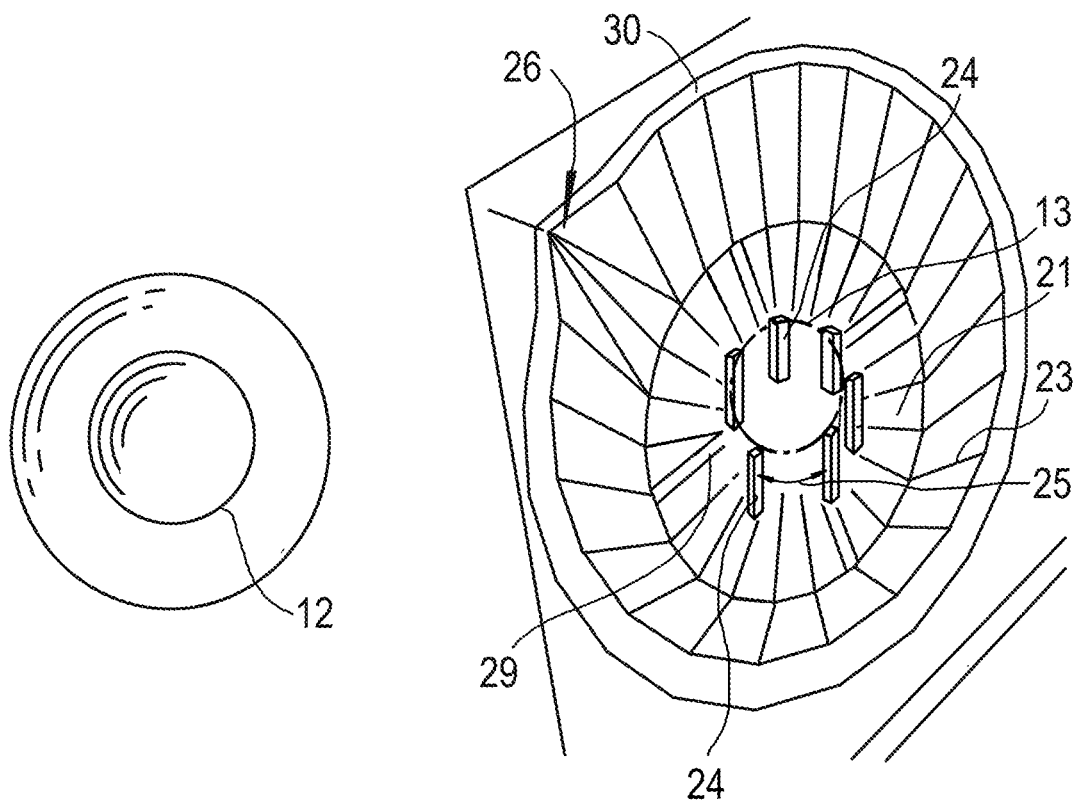
FIG. 2 is a top view of the contact lens storage container shown in FIG. 1.

The storage container 10 comprises at least one well 20 configured as a receptacle for the contact lens 11; the at least one well 20 and respective contact lenses 11 exist in a 1:1 ratio, i.e. there is only one lens 11 per well 20. The well 20 is formed with a base wall 21 preferably configured as a substantially disc-shaped reception area and a side wall 23 preferably configured as an upwardly sloping peripheral wall. It should be understood that the well 20 can have any three-dimensional configuration that is suitable for housing a contact lens 11. In an example of the present invention the side wall 23 is angled such that, together with the base wall 21, the well 20 forms a generally concave depression as seen in FIG. 2. The well 20 is filled with a suitable storage solution 15 to keep the stored contact lens 11 from drying out, commonly and preferably saline.

Figure 3A:
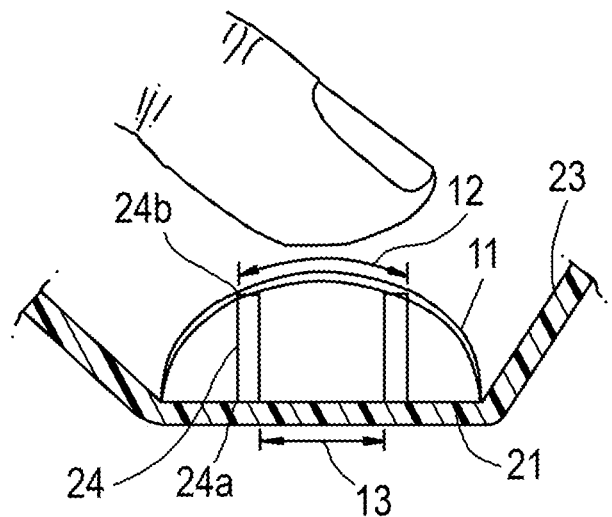
FIG. 3 (*a* to *c*) shows the steps in picking up a contact lens from the contact lens storage container according to an example of the present invention.
Figure 3B:
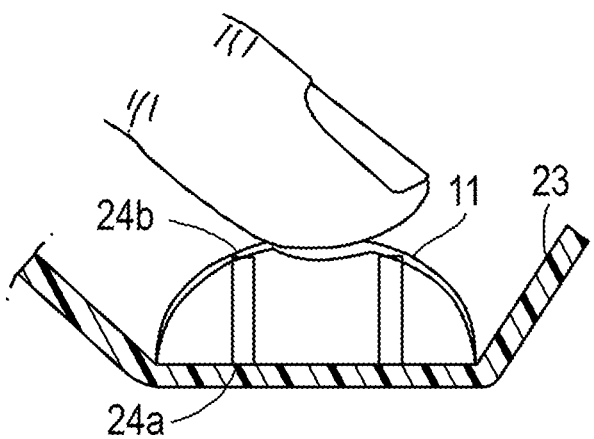
Figure 3C:
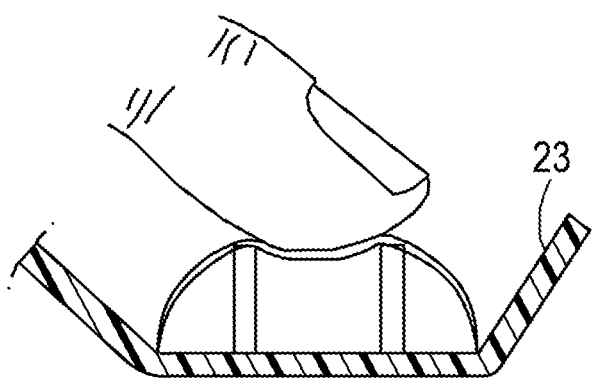

Within the well 20 is fabricated a support structure 24. In the particular embodiment of the present invention, the structure is an upstanding member 24 and behaves as a pillar or pedestal for supporting the concave surface of a contact lens 11; the member 24 can be formed separately and then mounted to the well 20 or it may be integral to the well 20 and produced during the injection moulding process. The member 24 extends outwardly or upwardly from a first end 24*a* attached to the interior side of the base wall 21 to a second end 24*b* opposite the first end 24*a* so as to provide a support to a contour of the concave corneal contact surface of the contact lens 11. The member 24 is configured to control a contact surface area 12 between the contact lens 11 and an applicator tool (not shown) e.g. a user's finger or mechanical device. The perimeter of the member 24 defines a depression area 13 such that the contact lens 11 is left unsupported by the depression area 13 as shown in FIG. 3*a*. However, the depression area 13 can also comprise a weak deformable area of the support structure 24 under the influence of finger pressure, e.g. deformable ribs. To fulfil this requirement, the member 24 is in an example of the present invention configured to be substantially cylindrical or ring-shaped as shown in FIG. 2. The contact surface area 12 between the contact lens 11 and applicator tool (e.g. the index finger) is dictated by the area defined by the perimeter of the member 24. When the convex surface of the contact lens 11 is depressed by a user the lens 11 is advantageously encouraged to deform about the second end 24*b* of the member 24 such that surface area of the lens 11 in contact with the user increases until the area defined by the perimeter of the member 24 prevents any further increase in the contact surface area 12 between the applicator tool and the contact lens 11 as shown in FIG. 3*b* and FIG. 3*c*. Thus, the second end 24*b* of the member 24 acts like a fulcrum 106 such that the contact lens 11 is encouraged to pivot about the fulcrum 106 such that the contact surface area 12 deforms when pressure is applied to the portion of the contact lens 11 in the depression area 13.

Inversion of the contact lens 11 will result in the periphery or rim of the contact lens 11 to sweep about an arc. However, the side wall 23 of the well 20 is angled such that the periphery or rim of the contact lens 11 is resisted from lifting by contacting a point on the side wall 23 of the well 20. As the rim of the contact lens 11 is resisted from lifting away from the base wall 21, the portion 12 of the contact lens 11 in the depression area 13 is made to deform. As the contact surface area 12 of the contact lens 11 increases, the surface tension increases between the applicator tool and the contact lens 11. Thus the area defined by the perimeter of the member controls the contact surface area 12 between the applicator tool and the contact lens 11 which ultimately controls the degree of surface tension between the applicator tool and the contact lens 11. In the particular example of the present invention shown in FIG. 3, the member 24 is positioned in the well 20 such that the depression area 13 is directly aligned with the apex of the contact lens 11. This allows the apex of the contact lens 11 to be in contact with the finger. If a different portion of the contact lens 11 to be in contact with the finger causing the contact lens 11 to be off center on the finger, there is a tendency that the contact lens 11 may not be correctly located on the corneal surface when offered up to the eye. In an extreme case, the contact lens 11 is orientated off-centre on the surface of the finger causing the edge of the contact lens 11 to touch the surface of the eye when offered up to the eye resulting in an undesirable folding of the contact lens 11 on the finger. In some cases, the user has to rotate the finger to make sure that the concave side of the contact lens 11 faces the corneal surface of the eye. Without a mirror or image of the eye, the process of applying the contact lens 11 to the eye becomes very difficult or near impossible. Thus, properly positioning of the contact lens 11 over the depression area 13 is important to make sure that the finger protected by the film of the present invention comes into contact with the correct portion of the contact lens 11 (e.g. apex portion of the contact lens) over the depression area 13 so as to allow the contact lens 11 to lie centrally on the finger. This ensures that the apex of the contact lens 11, more particularly the concave side of the contact lens 11 to align with the corneal surface of the eye. To correctly position the contact lens 11 over the depression area 13, preferably centrally over the depression area 13, the side walls 23 of the well 20 functions as a guide that is capable of engaging the contact lens 11 edge when a contact lens 11 is inserted into the well 20 and to urge the contact lens 11 to lie within a defined location over the depression area 13, ideally centrally over the depression area 13. Thus, when a lens 11 is inserted off-centre of the defined location by more than a permitted tolerance, the guide urges the lens 11 towards the centre of the support structure 24. According to the present invention, the permitted tolerance is anywhere between Xmm to Ymm, preferably, Zmm to Wmm from the axial centre of the contact lens 11. Beyond the permitted tolerance the contact lens 11 is classed as being off-centre over the depression area 13, resulting improper positioning of the contact lens 11 on the finger.

The size of the depressed area 13 is important because if it is too small the surface tension between the finger and contact lens 11 will not be greater than between the contact lens 11 and the support. If, however, the depressed area 13 is too large then the lens 11 is at risk of collapsing or inverting. The optimum ratio is such that the surface tension of the part that is depressed is large enough for it to adhere to the finger and the surface tension of the periphery holds the lens 11 in place in the correct orientation. The depression area 13 optionally has an area in the range 5 mm$^2$ to 180 mm$^2$, preferably 78 mm$^2$.

The contact lens 11 deforms to the shape of the contact point of the applicator tool as shown in FIG. 3*c*. The result of the increase in surface tension is that it becomes possible to remove the contact lens 11 from the well 20 whilst also decreasing the chance of dropping the contact lens 11 when offering and during subsequent application of the contact lens 11 to the eye. The outwardly extending side wall 23 of the well 20 allows the contact lens 11 to be lifted free from the well 20 without fouling against the side walls 23 of the well 20. Uniquely, by supporting only one contour of the concave corneal contact surface of the contact lens 11, the entire contact lens 11 does not undergo deformation under the pressure of the applicator tool due to the second end 24*b* of the support member 24 preventing the deformation actioned on the contact surface area 12 transmitting to the outer periphery, or rim of the contact lens 11; deformation is limited to the area of the contact lens 11 directly above the depression area 13 and is arrested to the location of the contour on the contact lens 11. The advantage of this is that the surface tension between the contact lens 11 and the applicator tool is optimised such that it is great enough that the contact lens 11 can easily overcome the adhesion of lens 11 to support member 24 whilst the tension is not so great as to impede the subsequent application to the eye. A further advantage of this optimisation is that during application of the contact lens 11, only one contact point on the surface of the lens 11 is required; critically, the contact point on the surface of the contact lens 11 that does not come into contact with the cornea; moreover, the area of the contact point is controlled and minimised and thus so is the risk of contamination.

Ventilation apertures or channels 25 are provided in the support structure 24 such that air may enter through the channels 25 during removal of the contact lens 11 to prevent the lens 11 from sticking to the well 20 or member 24. The channels 25 also prevent the storage solution 15 from being trapped within the support structure's 24 enclosure. Without the channels 25, a vacuum suction effect can be created during the depression of the contact lens 11 during removal, resulting in the contact lens 11 being made harder to remove thus increasing the amount of manipulation of the lens 11 required. Furthermore, the well 20 may comprise one or more raised ridges 29 and/or one or more depressions (not shown) so as to raise or elevate the contact lens 11 from the base wall 21 of the well. The one or more raised ridges 29 and/or one or more depressions are fixed to the interior side of the base wall 21 and create a path for fluid flow under and at the rim of the contact lens 11 so as to prevent against the vacuum suction effect being formed. Optionally the one or more raised ridges 29 are wedge shaped.

The support structure 24 can be configured in a number of designs including a solid structure (not shown), a hollow structure, a solid structure with one or more ventilation apertures (not shown). Whilst forming the support structure 24 as an upstanding standing annular ring has advantages in the ability to control the depression area 13 of the contact lens 11, the support structure 24 provides little support to the concave side of the contact lens 11 in an event that the contact lens 11 collapses. In an alternative embodiment of the present invention, the support structure 24 comprises a plurality of radially spaced apart fins 100 so as to provide ventilation channels 25 between the fins 100. Each of the fins 100 extends from one or more walls of the well 20 towards a depression area 13 similar to function of the depression area 13 discussed above with reference to FIGS. 3(a to c), whereby a portion of the contact lens 11 is left unsupported as shown in the storage container 10 of FIG. 3d and upwardly from the base wall 21 of the well 20. Where applicable the same references will be used to denote the same or similar features of the storage container 10 in FIGS. 3(a to c) and FIG. 3d. In the particular embodiment shown in FIG. 3d, each of the fins 100 has a major axis that radially extend to the side wall 23 of the well 20 and axially to the base wall 21 of the well 20. The fins 100 minimise the contact surface area between the contact lens 11 and the fins 100 and thereby, improve the releasability of the contact lens 11 seated on the plurality of fins 100 due to the reduced surface tension. Equally, as with the upstanding members 24 discussed above with reference to FIGS. 3(a to c), the plurality of fins 100 are spaced apart so as to provide ventilation channels 25 for storage fluid to escape and air to enter through the channels 25 between the fins 100 so as to maintain an equilibrium pressure acting externally and underneath the contact lens 11, i.e. to mitigate the vacuum suction effect.

Unlike the support structure 24 shown in FIG. 2, the second end 24d of each of the fins 100 opposite the first end 24c (the first end 24c being attached to the base wall 21 of the well 20) acts as a seat that is profiled to conform to the curvature of the concave surface of the contact lens 11, more specifically the second end 24d of each fin 100 comprises a first profile 102 that is contoured to generally conform to the curvature of the concave surface of the contact lens 11. Thus, unlike the support structure 24 in the earlier embodiment shown in FIG. 2, the plurality of fins 100 radially extending from the depressions area 13 provide additional and/or improved support to the concave side of the contact lens 11 and thereby, minimising the ability of the contact lens 11 to collapse onto the support structure 24, e.g. through the vacuum suction effect created during drainage of the contact lens 11 storage solution 15. Moreover, the fins 100 limits the contact surface area between the support structure 24 and the contact lens 11, so enabling the contact lens 11 to be lifted clear of the support structure 24 and thus, the storage container 10.

Instead of the side wall 23 of the well 20 forming a guide for urging the contact lens 11 centrally over the depressions area 13 (see FIG. 2), each of the plurality of fins 100 is profiled with a second profile 104 which functions as the guide that engages with the contact lens 11 edge and urge the contact lens 11 to lie over the depression area 13. The first profile 102 and the second profile 104 cooperate to form a seated region for supporting the concave side of the contact lens 11, i.e. the convex side of the contact lens 11 faces upwardly towards the wearer. This is clearly demonstrated in FIG. 3(e). The perpiphery or edge of the contact lens 11d engages with the guide 104 (second profile of the fin 100) so as to urge the contact lens 11 centrally over the depression area 13. In the normal rest position of the contact lens 11 (shown as a solid line in FIG. 3e), a portion of the contact lens 11a around the periphery of the contact lens 11 is supported by the first profile 102 of the fin 100. As shown in FIG. 3e the first profile 102 has a radius of curvature that generally conforms to the curvature of the concave side of the contact lens 11. However, it is not essential in the present invention that the radius of curvature of the first profile 102 to conform to the curvature of the concave side of the contact lens 11 but to generally support the curvature of the concave side of the contact lens 11 when seated on the fin 100. The portion of the contact lens 11b overhanging the fin 100 is left unsupported and represents the depression area 13. When pressure is applied to the unsupported portion 11b of the contact lens 11 overhanging the fin 100, the contact lens 11 deforms (shown by the dashed line 11c in FIG. 3e) about a fulcrum 106 on the fin 100. As shown in FIG. 3(e), the apex 12a of the contact lens 11 aligns with the centre of the depression area 13 denoted by the axis X-X. Thus, when picking up the contact lens 11 with the finger, the first point of contact with the contact lens 11 is in the apex region 12a of the contact lens 11. In a similar function to the side wall 23 shown in FIGS. 3(a to c), the second profile 104 engages with the periphery or edge of the contact lens 11 and so act to guide the contact lens 11 to lie within a permitted tolerance over the depression area 13. According to the present invention, the permitted tolerance is anywhere between ±0.5 mm to ±1.5 mm, preferably, −±1 mm from the central axis X-X or apex of the contact lens 11.

The second profile 104 can also limit the periphery or rim of the contact lens 11 from lifting when pressure is applied to the unsupported portion of the contact lens 11 in the depression area 13 (convex side of the contact lens around the apex of the contact lens) and thereby, preventing the contact lens 11 from inverting. FIG. 3f showing a side profile of an example of a fin 100 demonstrates how the shape of the fin 100 prevents the contact lens 11 from inverting when pressure is applied to the unsupported region of the contact lens 11 in the depression area 13. Further pressure on the depression area 13 of the contact lens 11 causes the periphery or rim of the contact lens 11 to lift further and pivot about the fulcrum 106. In absence of any resistance to prevent or limit the periphery or rim of the contact lens 11 from lifting, the periphery or rim of the contact lens 11a will sweep through an arc and eventually result in the contact lens 11 to invert on itself. By limiting the size of the depression area 13, and through surface tension between the periphery of contact lens 11a and the first profile 102 of the fin 100, lift of the periphery of the contact lens 11a is prevented as the centre is depressed.

To prevent or limit the periphery or rim of the contact lens 11d from lifting too far when pressure is applied to the depression area 13 of the contact lens 11, the second profile 104 cooperates with the first profile 102 of the fin 100 such that the distance X between a point 108 on the second profile 104 and the fulcrum 106 is less than or equal to the length Y of the contact lens 11 in contact with the first profile 102 (see FIG. 3e). When the distance X is less than or equal to the length Y, the rim of the contact lens 11 will contact a point 108 on the second profile 104 and thereby, is resisted from lifting further and thus, inverting when pressure is applied to the unsupported portion 12 of the contact lens 11 in the depression area 13. In the particular embodiment shown in FIG. 3e, the first profile 102 and the second profile 104 of the fin 100 cooperate at an angle. As the first profile 102 is curved, a tangental line on the first profile 102 meets the second profile 104 at an angle less than 90°.

Also shown in FIGS. 3(e and f), is a third profile 110 having an inclined surface that conforms to the curvature of the concave side 11c of the contact lens 11 when deformed in the depression area 13 (see dashed line in FIG. 3e). The third profile 110 may also function as a stop to prevent further deformation of the contact lens 11 in the depression area 13. The third profile 110 and the second profile 104 of the fin 100 cooperate to control the deformation of the contact lens 11 in the depression area 13.

Figure 3D:
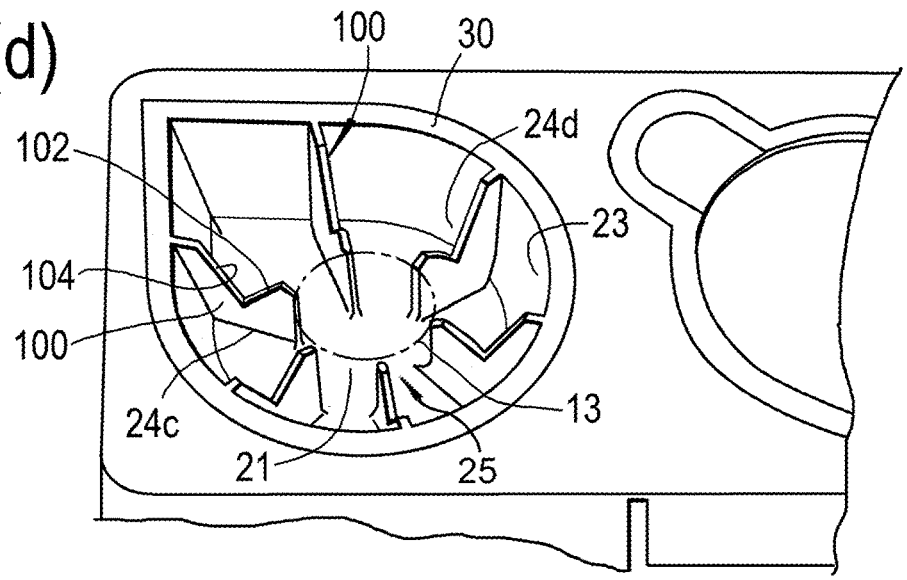
Figure 3E:
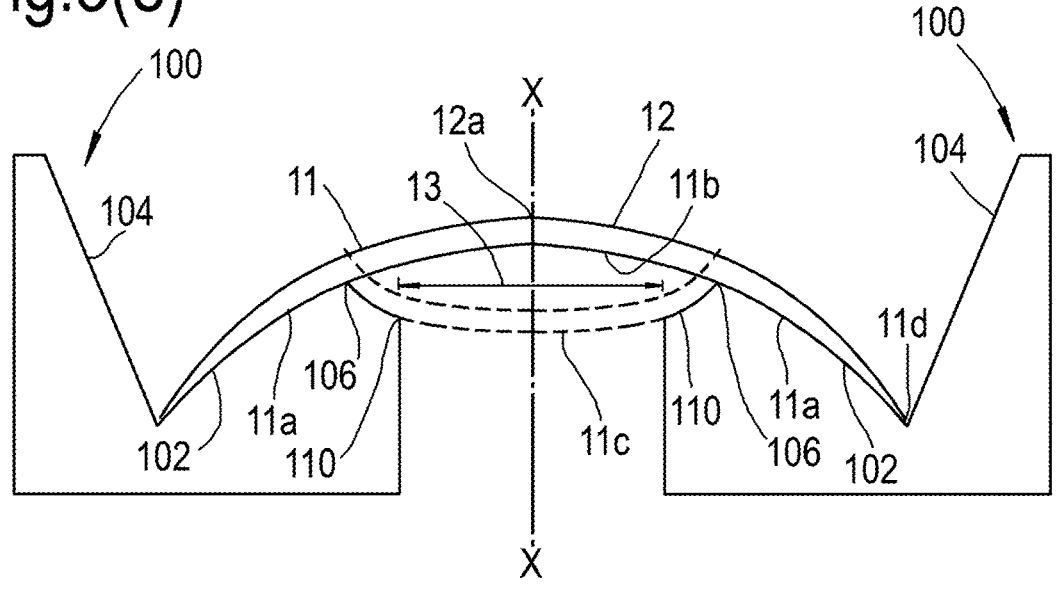
Figure 3F:
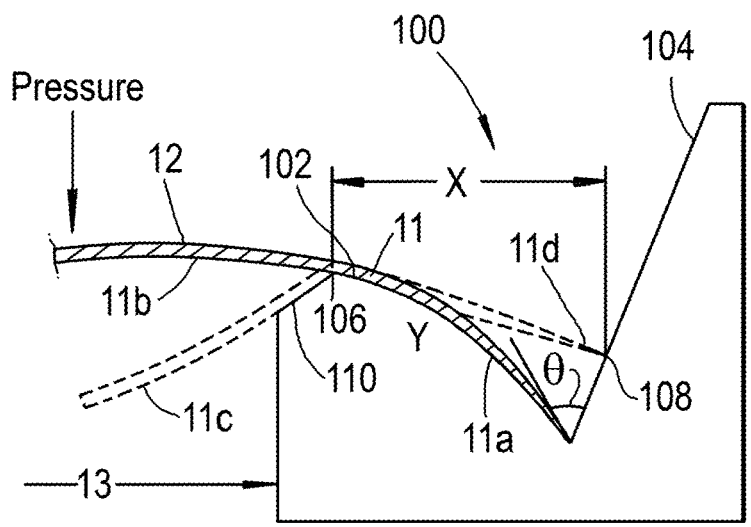

In both embodiments of the present invention shown in FIG. 2 and FIG. 3(d), the side wall 23 of the well 20 can preferably be configured with a spout 26, the spout 26 permits pouring of fluid from the well 20, in particular the storage solution 15.

The storage container 10 is fabricated with a flange 30, the flange 30 is configured to sealingly engage with a closure or cover (or lidstock) 31 which is typically a metallic foil or foil/plastic laminate as commonly known in the art such that the storage container 10 and importantly the well 20 is made fluid-tight. The flange 30 is therefore preferably situated around the periphery of the well 20 or the storage container 10; the flange can either be a solid protrusion or an adhesive. For disposable contact lens storage containers, the cover 31 is typically metallic foil and the seal is applied during packaging and sterilisation to conform to industrial standard requirements. For re usable contact lens storage containers, the cover 31 is a removable and replaceable structure that engages with the flange 30 of the storage container 10; by for example, a snap fit or interlocking thread in the cover and the storage container 10.

An additional advantage associated with this storage container 10 for contact lenses 11 is that the contact lens 11 is held in the correct orientation for insertion into the eye without further manipulation. The reduction of manipulation results in lowered risk of contamination.

According to a second independent aspect of the present invention, the applicant has provided at least one terminally sterilised disposable applicator film 45 housed within a contact lens applicator container 50 for a contact lens 11 as seen in FIG. 4. The applicator container 50 is optionally a pouch (not shown) comprising a metallic foil or foil/plastic laminate. Alternatively, according to an example of the present invention, the applicator container 50 can be fabricated individually or as part of blister pack packaging (not shown) comprising a plurality of applicator containers 50. The applicator container 50 is fabricated of a material with a high stiffness whilst being capable of limited plastic deflection and water-tight; typically this can be a plastic. The applicator container 50 can be manufactured with any suitable means known in the art, the most typical being injection moulding.

Figure 7:
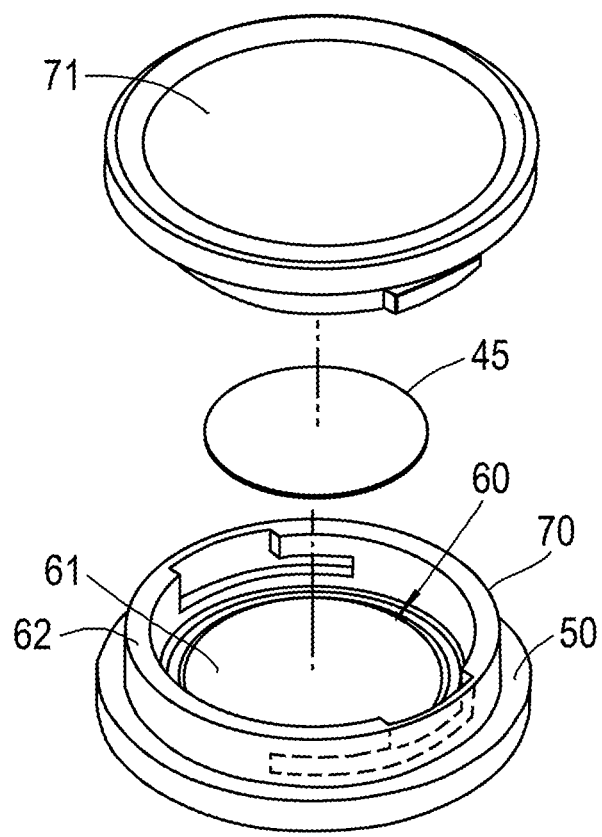
FIG. 7 is a schematic view of a contact lens applicator storage container housing a contact lens applicator film according to another example of the present invention.

The applicator container 50 comprises at least one recess 60 configured as a receptacle for the applicator film 45. In an example of the present invention, recesses 60 and applicator films 45 exist in a 1:1 ratio, i.e. there is one applicator film 45 in each recess 60 as shown in FIG. 4. It should however be appreciated that if the recess 60 is sufficiently large it is possible for a plurality of applicator films 45 to be housed in one recess 60 as shown in FIG. 7. The recess 60 is formed of a base wall 61 and a side wall 62. It should be understood that the recess 60 can have any three-dimensional configuration that is suitable for housing the disposable applicator film 45. The recess 60 is preferably larger than the disposable applicator film 45 however it is also more preferable that the recess 60 is not substantially larger than the disposable applicator film 45 such that applicator containers 50 can be efficiently packed together.

The applicator container 50 is fabricated with a flange 70, the flange 70 is configured to sealingly engage with a closure or cover 71 which is typically a metallic foil or foil/plastic laminate such that the applicator container 50 and importantly the recess 60 is made fluid-tight as shown in FIG. 5 and FIG. 7. The flange 70 is therefore preferably situated around the periphery of the recess 60 or the applicator container 50. For disposable applicator films 45, the cover 71 is typically metallic foil and the seal is applied during packaging and sterilisation to conform to industrial standard requirements. For the example of a multi-use applicator container 50 as shown in FIG. 7, the cover 71 is a removeable lid suitable for sealing the applicator films 45 into the container for storage. The seal can be any seal to prevent the ingress of fluids, solids or any matter that may contaminate the applicator films 45 for example a rubberised seal.

The disposable applicator film 45 provides a flexible and protective barrier between the applicator tool such as an index finger and the contact lens 11 and is configured as a thin film 46 as shown in FIG. 6. The film 45 is preferably sized such that when applied it covers an area of the applicator tool greater than that in contact with the contact lens 11. The film 45 comprises an adhesive coating 47 on at least a portion of one side 46a of the film 45 (illustrated in the enlarged portion of FIG. 5a). To maintain the tackiness of the adhesive coating 47 on the applicator film 45, a protective layer or backing (e.g. silicone coated layer) 44 can be applied on the adhesive coating 47 for when it is ready to be used. The protective layer 44 can comprise a tab 44a as shown in FIG. 5a that allows the wearer to easily peel the protective layer 44 exposing the adhesive coating 47 underneath without the need to touch and possibly contaminate the adhesive coating 47 and/or the applicator film 45 compromising its sterility.

Equally both opposing sides of the film 45 comprises an adhesive coating 47. The film 45 is sufficiently flexible to conform to the shape of the depression area 13 of the application tool, e.g, the curvature of the surface of the index finger. Typical materials of the film 45 include but are not limited to silicone or even other plastic materials having suitable deformability to conform to the shape of an applicator tool, e.g. finger. Preferably, the adhesive is environmentally friendly and should not pose a health risk if ever the adhesive comes into contact with the eye. Typically the adhesive is an acrylic based adhesive, preferably a water based acrylic adhesive. Commercially available films with an adhesive coating on the market include but are not limited to: ClearFilm IV, IV3000, Tegaderm and Opsite. The applicator film 45 has sufficient flexibility to not impede the dexterity or the touch-sensitivity of the applicator tool. Optionally the film 45 is disk shaped as shown in FIG. 6a and has a diameter of 5 mm to 30 mm, preferably the diameter of the film 45 is 22 mm. Alternatively the film 45 may be an ellipse as shown in FIG. 6b to increase the surface area coverage of the finger (i.e. maps the shape of the finger tip) where the minor axis has length in the range 11 mm to 27 mm preferably 19 mm; and the major axis has length in the range 15 mm to 30 mm preferably 19 mm. This limits the possibility of an unprotected part of the finger coming into contact with the contact lens 11 as more of the finger is covered by the applicator film 45 of the present invention. As the applicator film 45 is a disposable item, it can also be made bio-degradable once discarded.

In an example of the present invention as shown in FIG. 6a, the at least one side 46a of the film 45 comprises an inner portion and an outer portion, wherein the inner portion comprises the adhesive coating 47 and the outer portion is free from the adhesive coating 47. Additionally the outer portion can comprise a tab 45a as shown in FIG. 6b for handling the film 45 without contact with the adhesive coating 47 or for removing/peeling the applicator film 45 from the applicator tool (e.g. finger) as shown in FIG. 6b. The film 45 is installed into the well 60 such that the at least one side 46a with adhesive coating 47 is orientated such that the adhesive coating 47 is exposed or presented to the user when the cover 71 is removed i.e. it faces away from and is not in contact with the base wall 61 of the recess 60. The film 45 and/or applicator container 50 can be coloured, opaque or transparent so as to aid in the film 45 being easily identifiable by the user. Optionally, as an indication of the sterility of the film 45 and/or applicator container 50, the film 45 and/or applicator container 50 can be coloured with an ink that reacts to the sterilisation status of the film 45 and/or applicator container 50. For example, the colour of the film 45 changes when exposed to certain bacteria that are harmful to the eye. This will give an indication to the user that the film 45 and/or applicator container 50 is contaminated prior to its usage. It can also provide an indication of the cleaniness of the applicator tool, e.g. finger, so providing further reassurance of the need to protect the contact lens 11 from contaimination by the applicator tool (finger).

Alternatively, the adhesion to the applicator tool is attained by only electro-static forces between the film 46 and the applicator tool when contact is made such that no adhesive coating 47 is required.

The recess 60 is fabricated such that it has sufficient depth so as to prevent the film's 45 adhesive coating 47 from contacting the under surface of the cover 71. In an example of the present invention the cover 71 is the protective layer 44. The film 45 is mounted to the recess 60 such that it does not become detached from the recess 60's base wall 61. The film 45 may be held to the base wall 61 through electro-static attraction between the base wall 61 of the recess and the film 45. This attraction is suitable for short-term storage of the applicator film 45 in the container 50. To prevent the film 45 from moving around within the recess 60 during long-term storage and transport of the applicator film 45, it is beneficial to optionally provide means for securing the film 45 to the base wall 61 of the recess 60. These means are inclusive of but are not exclusively limited to use of a mechanical retainer, for example, a clip, or an intermediate layer 48 on the base wall 61 of the recess 60. In an example of the present invention, the base wall 61 of the recess can comprise a pressure sensitive adhesive, such that whilst the film 45 is mounted on the base wall 61 it adheres but when the film 45 is removed from the base wall 61, the adhesion is easily overcome.

In an example of the second independent aspect of the present invention shown in FIG. 5a, the intermediate layer 48 is mounted to the base wall 61 of the recess 60. In one example of the present invention there is one intermediate layer 48 per film 45 present in the recess 60. It should be understood however, if more than one film 45 were included in each recess 60 then one intermediate layer 48 can service a plurality of films 45. The intermediate layer 48 comprises a first adhesive 49a on one side 48a of the intermediate layer 48 in contact with the base wall 61 of the recess 60 and a second adhesive 49b on the opposite side 48b. In the particular example of the present invention, the first adhesive 49a is stronger than the second adhesive 49b such that on removal of the film 45 from the recess 60, the intermediate layer 48 is not removed from the container 50 in the same motion. Preferably, according to an example of the present invention, the second adhesive 49b is a low-tack pressure sensitive adhesive.

To accommodate the intermediate layer 48 in the container 50 without jeopardising the volume in the container and thus, to ensure that the adhesive layer on the applicator film 45 does not touch or come into contact with the underside of the cover 71 when no protective layer 44 is positioned within the container, the recess 60 further comprises a depression 64. The depression 64 is shaped to accommodate the intermediate layer 48 such that the second adhesive 49b is flush with respect to the upper surface of the base wall 61a as shown in FIG. 5b. Preferably, the depression 64 has a surface area less than the surface area of the film 45, thus removing the possibility of adherence of the applicator tool to the base wall 61 of the recess 60 and further facilitating detachment of the film 45 from the recess 60.

The nature of a low-tack, pressure-sensitive second adhesive 49b permits the film 45 to be bonded in the recess 60 with sufficient force to retain it whilst allowing it to be lifted when being removed, leaving no adhesive residue adhered to the film 45 that could be transferred to the contact lens 11. In an alternative option of the present invention, one side of the intermediate layer 48 is attached to base wall 61 by the first adhesive 49a, the other side of the intermediate layer 48 comprises a release agent to allow the film 45 to be transferred from the intermediate layer 48 to the applicator tool, common examples are polyvinyl alcohol, crosslinkable silicone, or materials that have a low surface energy.

Figure 8:
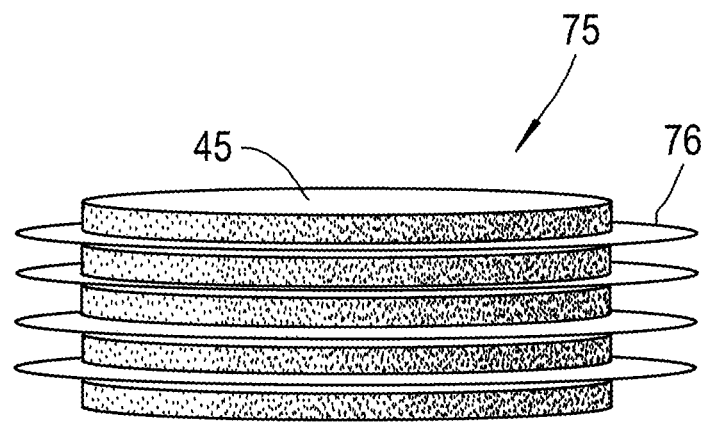
FIG. 8 is a cross-sectional view of a contact lens applicator film stack assembly according to an example of the present invention.
Figure 9A:
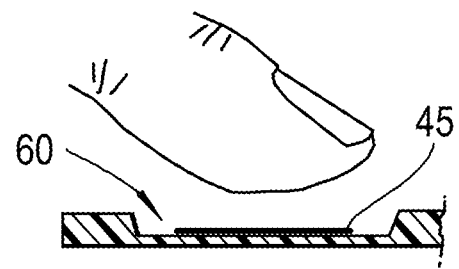
FIG. 9 (*a* to *d*) shows the steps in picking up a contact lens applicator film from the contact lens applicator film container shown in FIG. 5.
Figure 9B:
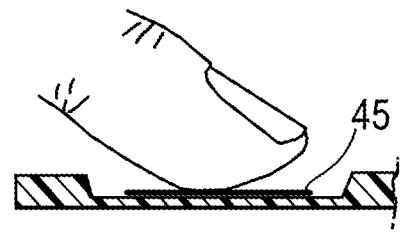
Figure 9C:
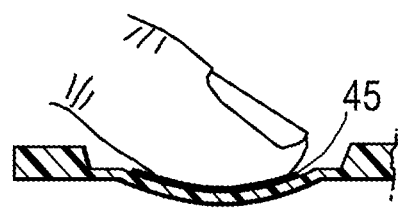
Figure 9D:
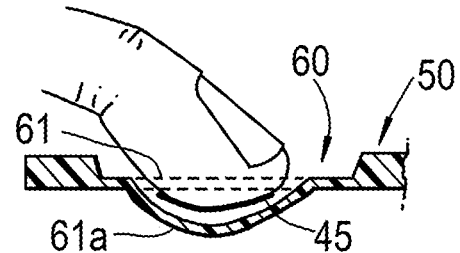
Figure 9E:
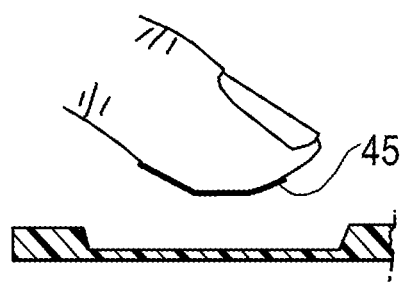

In an example of the present invention, one or more disposable applicator films 45 are provided in a stack assembly 75 as shown in FIG. 8. The stack assembly 75 further comprises at least one or more strips of release material 76 spaced between adjacent one or more disposable applicator films 45 such that the films 45 do not stick together so as to prevent adhesive residue being deposited on the surface of each film 45 that is in contact with the contact lens 11 during handling. In a further example of the present invention, one or more applicator films 45 are arranged on a single strip of release material 76, the strip of release material 76 is folded such that adjacent applicators 45 on the strip 76 overlay one another. The stack assembly 75 can be inserted into the contact lens applicator container 50 as shown in FIG. 7.

To lift the film 45 from the container 50, a user only has to press the contact portion of an applicator tool (e.g. finger) onto the at least one side 46a of the film 45 having the adhesive coating 47 as shown in FIG. 9. In the particular embodiment of the present invention shown in FIG. 9, an index finger is used as the applicator tool and the pad of the index finger is the contact portion. A rolling action of the finger can help to ensure maximum coverage of the pad of the finger with the adhesive coating 47 of the film 45 and thereby ensure maximum coverage of the finger by the sterile applicator film 45. To limit or remove the need to roll the finger over the adhesive coating 47 of the applicator film 45, the base wall 61 of the recess 60 for accommodating the applicator film 45 can deform under the application of finger pressure so as to conform the contour of the finger as shown in dashed lines 61a in FIG. 9(e). This allows the applicator film 45 to conform to the contour of the finger so ensuring maximum coverage of the adhesive coating 47 of the applicator film 45 to the finger. The base wall 61 of the recess 60 can be fabricated with any deformable material known in the art, e.g. rubber or plastics. For efficiency savings during manufacture, the base wall 61 of the recess 60 can be made thinner than the rest of the applicator container 50 allowing it to deform under the application of finger pressure.

Figure 10B:
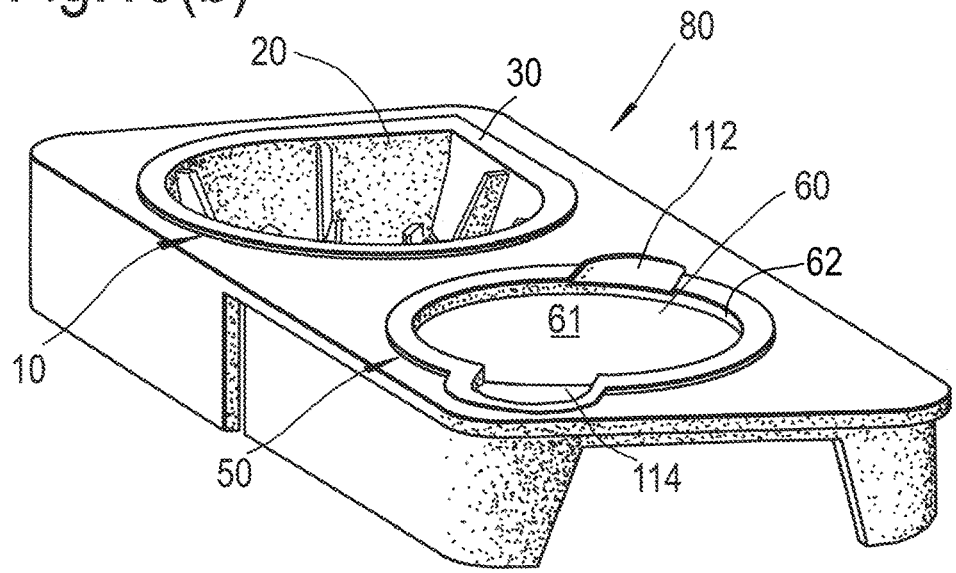
FIG. 10(*a*) is a cross-sectional view of a kit comprising a contact lens applicator film and contact lens storage container according to an example of the present invention.

The adhesive characteristic of the film 45 is such that for removal from the applicator tool, a user can simply peel it off without a dedicated solvent solution being required. The film 45 is then discarded. The disposable film applicator 45 provides a means for a user to insert a contact lens 11 without contaminating it through contact and without compromising on the dexterity of the applicator tool (e.g. finger). This results in a user being able to handle a contact lens 11 under many conditions as sterility is provided by the applicator film 45 even though the user is not required to perform a thorough washing of their applicator tool, for example, they are not required to perform a thorough washing of their hands before application or removal of the lens 11. More importantly, the applicator film 45 is thin enough so as to not entirely remove the sense of touch of the pad of the finger when picking up the contact lens 11 and applying the contact lens 11 onto the eye. The applicator film 45 helps to keep to the traditional means to apply the contact lens 11 to the eye using the finger whilst ensuring the sterility of the contact lens 11, i.e. to prevent microbial, mechanical and/or chemical contamination of the contact lens 11 by direct contact with the finger itself. Maintaining or limiting the loss of sense of touch of the finger protected by the applicator film 45 is important to ensure the correct positioning of the contact lens 11, particularly the apex of the contact lens 11 on the corneal surface of the eye. In some cases, the wearer makes adjustments to the contact lens 11 when placed on the eye, e.g. by sliding the contact lens 11 on the surface of the eye so that that the contact lens 11 is in registration with the corneal surface of the eye, i.e. the portion of the eye that receives light to be focussed. Whilst a majority of wearers use a mirror to help guide the contact lens 11 on the corneal surface, in some instances particularly in a sporting environment, the wearer relies on the sense of touch to apply the contact lens 11. This sense of touch may prove vital in the ability to correctly position the contact lens 11 on the surface of the eye. Without this sense incorrect positioning of the contact lens 11 on the eye may result increasing the risk of the contact lens 11 migrating under the eyelid To combine the benefits of the storage container 10 of the present invention and the applicator film 45 of the present invention, it should be appreciated that the contact lens storage container 10 of the present invention need not be supplied separately to the applicator container 50, they can be provided in combination as shown in FIG. 10(a) as a kit. In this example, the contact lens 11 and the disposable applicator film 45 are housed in their respective well 20 and recess 60 that are located on a single body combined container 80. The container 80 is of the same type and construction as those described above. At least one flange (not shown) is configured to sealingly engage with at least one closure or cover (81) which is typically a metallic foil or foil/plastic laminate such that the the well 20 and/or recess 60 are made air and fluid tight to prevent contamination and fluid loss. The at least one flange is therefore preferably situated around the periphery of the well 20 and recess 60 of the container 80. The at least one cover 81 is typically metallic foil and the seal is applied during packaging to conform to industrial standard requirements. It should be understood that both the well 20 and the recess 60 can be covered by the same cover—having the same material to cover both the recess 60 and the well 20 or by having different material to cover the recess 60 (e.g. a plastic) and the well 20 (e.g. metallic foil)—or by separate covers—having the same materials or different.

Figure 10C:
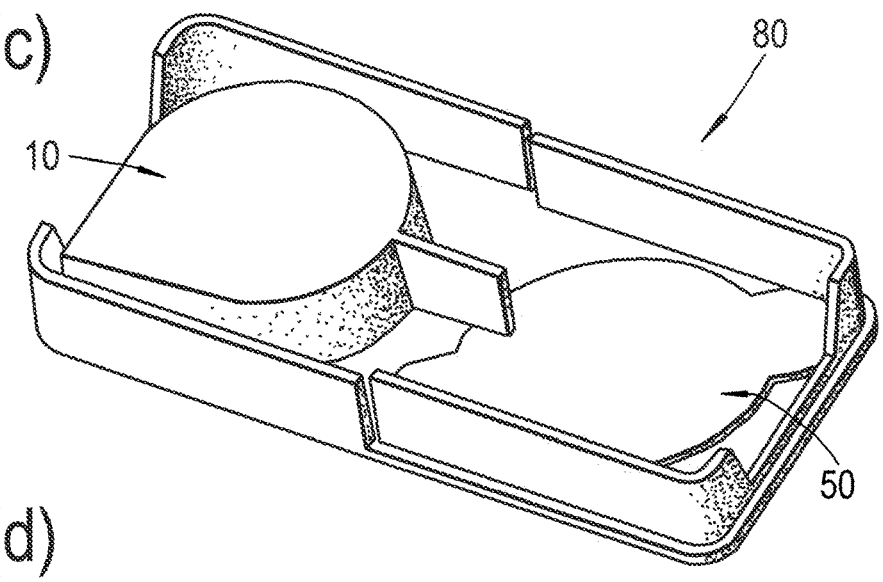
Figure 10D:
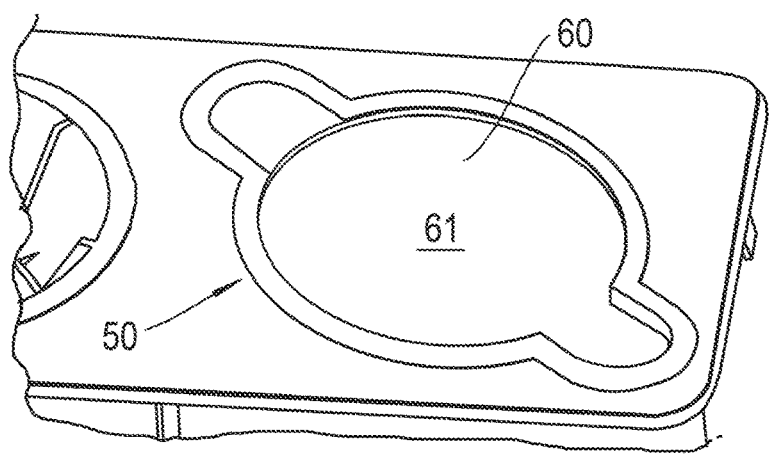

An example of the combined contact lens storage container and the applicator container formed as a kit with the top cover, or the lidstock, removed is shown in FIGS. 10 (b and c). The kit 80 can be fabricated as a single body, e.g. by injection moulding. The recess 60 for accommodating the applicator film 45 is much shallower than the well 20 for accommodating the contact lens 11. As discussed above, the base wall 61 of the recess 60 can fabricated to deform under the application of finger pressure so as to ensure that there is adequate coverage of the adhesive coating 47 of the applicator film 45 onto the applicator tool (e.g. finger). When fabricating the kit 80 as a single body, the thickness of the base wall 61 can be made thinner than the rest of the kit 80 allowing the base wall 61 to deform under the influence of pressure from a finger. Also shown in FIGS. 10 (b and c), are two further depressions 112, 114 adjacent or at the circumferential edge of the recess 60 for accommodating the applicator film. The depressions are optional and are sized to accommodate the tabs 44a and 45a of the applicator film 45 and the layer 44 for protecting the adhesive coating 47 on the applicator film 45 respectively discussed above. The depressions 112, 114 are shown to have different depths (see FIG. 10d). The shallower depression 112 accommodates the tab 44a for removing the protective layer 44 to expose the adhesive coating 47 of the applicator film 45 underneath and the deeper depression 114 accommodates the tab 45a for handling the applicator film 45 of the present invention, in particular for peeling a used or expended applicator film 45 from the applicator tool (e.g. finger) to be discarded.

Four steps are used, as shown in the flow diagram FIG. 12 and illustrated in FIG. 11, to apply a contact lens 11 to the cornea of a user's eye, as housed in the contact lens and applicator film combined cartridge 80.

The user removes the cover (81) which is typically a metallic foil or foil/plastic laminate, exposing the contact lens storage well 20 and contact lens applicator film 45.

Figure 11A:
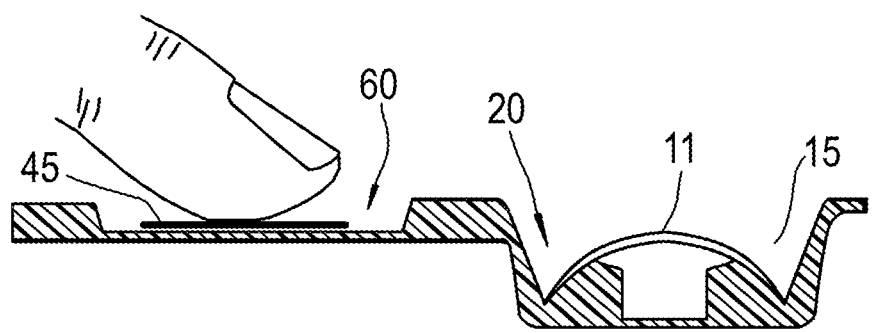
FIG. 11 (*a* to *d*) shows the steps in picking up a contact lens from the kit shown in FIG. 10.
Figure 11B:
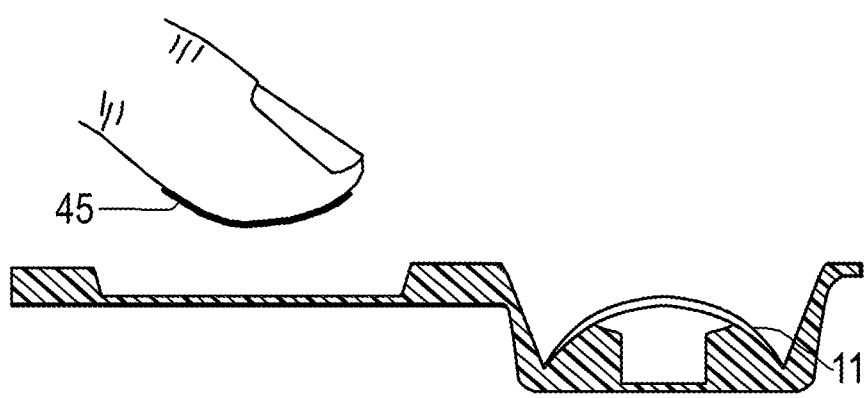

Step 94 is optional and involves draining and discarding the storage solution 15 from the contact lens well 20.

Where an additional protective cover 44 is supplied over the applicator film 45, this is removed by pulling tab 44*a* to expose the adhesive layer of the applicator film 45. A user then presses the contact portion of the applicator tool to the film 45 until adhesion is induced between the film 45 and the tool as shown in FIGS. 11*a* and 11*b* (Step 93). In the particular embodiment shown in FIG. 11, the user presses and/or rolls down on the applicator film 45 using their index finger. Steps 93 and 94 may be performed in any order however, to ensure that sterility of the film 45 is maintained and to avoid any inadvertent contamination of the lens 11 it is advantageous to drain the storage solution 15 from the well prior to removing any protective layer 44 and to adhereing the film 45 to the finger.

Figure 11C:
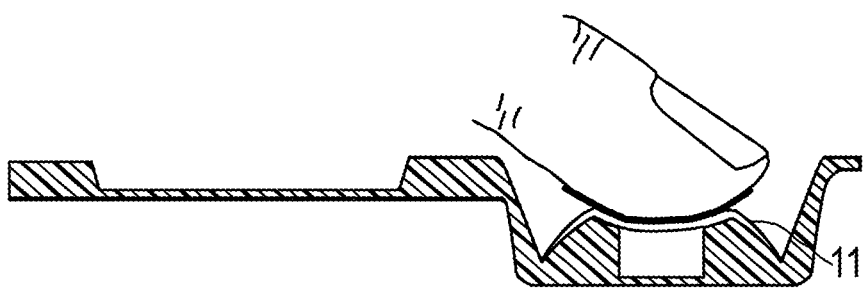
Figure 11D:
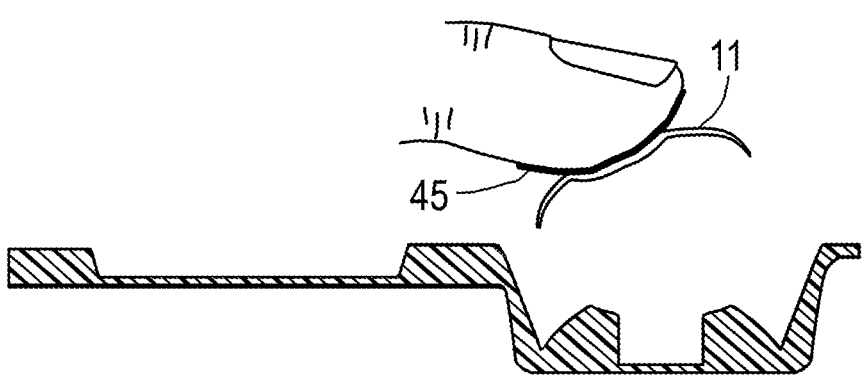

The user then gently presses or touches the film 45 to the convex surface of the contact lens 11 to permit slight deformation of the contact lens 11 and cause the contact lens 11 to adhere to the applicator film 45 as a result of the surface tension due to the solution 15 residue left on the contact lens 11 as shown in FIG. 11*c* (step 95). As the contact lens 11 is generally centrally located over the depression area 13 of the support structure 24, the contact lens 11 is lifted from the storage well 20 and is in the correct orientation to be applied to the cornea without further manipulation.

The contact lens 11 is brought into contact with the cornea and inserted into the eye. The contact lens 11 is released by the applicator film 45 because the surface tension between the contact lens 11 and the cornea is greater than the surface tension between the contact lens 11 and the applicator film 45. The applicator film 45 is removed from the applicator tool and discarded (step 96), e.g. using the tab 45*a* discussed above.

Changes and modifications, addtions and deletions or material or adhesive type may be made to the different examples given above without departing from the scope of the invention as defined in the claims.

The invention claimed is:

1. A storage container for contact lenses comprising:
   at least one well for receiving a contact lens and a storage liquid, the well having a floor;
   a support structure for holding the contact lens in a defined location above the floor of the well, the defined location comprising a lens depression area that in use permits depression of the contact lens under finger pressure, wherein the support structure comprises a plurality of spaced apart fins extending from one or more walls of the well; and
   a guide capable of engaging a contact lens edge when the contact lens is inserted into the well and to urge the contact lens to lie within the defined location and over the lens depression area.

2. The storage container of claim 1, wherein the lens depression area comprises an unsupported portion of the support structure and the guide urges the contact lens centrally over the lens depression area.

3. The storage container of claim 1, wherein each of the plurality of spaced apart fins cooperate to comprise the guide.

4. The storage container of claim 1, wherein each of the plurality of spaced apart fins comprises a first profile for supporting a concave surface of the contact lens and a second profile for guiding the contact lens over the lens depression area, and wherein the first profile allows the contact lens to deform about a fulcrum when finger pressure is applied to a portion of the contact lens in the lens depression area.

5. The storage container of claim 4, where the first profile extends between the fulcrum and the guide such that a distance between a point on the guide and the fulcrum is less than or equal to a length of the contact lens that is in contact with the first profile.

6. The storage container of claim 4, wherein each of the plurality of spaced apart fins comprises a third profile adjacent the fulcrum that engages with an underside of the contact lens when the contact lens is depressed in the lens depression area.

7. The storage container of claim 1, further comprising:
   at least one contact lens applicator film for picking up the contact lens and applying the contact lens to an eye, the at least one contact lens applicator film comprising:
      a sterilised film; wherein at least a portion of at least one side of the contact lens applicator film comprises an adhesive coating that is arranged for adhering to a surface of a finger such that, in use, when applying the contact lens to the eye a user can pick up the contact lens applicator film with the finger and subsequently pick up the contact lens using the finger protected by the contact lens applicator film.

\* \* \* \* \*